United States Patent [19]

Koenig et al.

[11] 4,189,446

[45] Feb. 19, 1980

[54] MANUFACTURE OF α-HALOETHYLCARBAMYL HALIDES

[75] Inventors: Karl-Heinz Koenig, Frankenthal; Christian Reitel, Heidelberg, both of Fed. Rep. of Germany

[73] Assignee: BASF Aktiengesellschaft, Fed. Rep. of Germany

[21] Appl. No.: 921,174

[22] Filed: Jul. 3, 1978

[30] Foreign Application Priority Data

Jul. 16, 1977 [DE] Fed. Rep. of Germany ....... 2732284

[51] Int. Cl.² .............................................. C07C 51/58
[52] U.S. Cl. ................................. 260/544 C; 424/315
[58] Field of Search .................................... 260/544 C

[56] References Cited

PUBLICATIONS

Bull. Soc. Chim. Belg. vol. 65, pp. 291–296 (1956).

*Primary Examiner*—Gerald A. Schwartz
*Attorney, Agent, or Firm*—Keil & Witherspoon

[57] ABSTRACT

Novel α-haloethylcarbamyl halides and a process for their manufacture by reacting vinyl isocyanate with a hydrogen halide.

The α-haloethylcarbamyl halides, especially α-chloroethylcarbamyl chloride, prepared by the process of the invention, are valuable starting materials for the manufacture of surface-coating raw materials, textile coatings, dyes, drugs and crop protection agents.

5 Claims, No Drawings

MANUFACTURE OF α-HALOETHYLCARBAMYL HALIDES

The present invention relates to a process for the manufacture of α-haloethylcarbamyl halides by reacting vinyl isocyanate with a hydrogen halide.

Angewandte Chemie, 74 (1962), 848–855 discloses the reaction of alkylcarbamyl chlorides with elementary chlorine to give the corresponding α-chloroalkylcarbamyl chlorides. However, the products which result are mixtures, both in respect of the degree of halogenation and in respect of the position of the halogen atoms entering the molecule. The process is unsatisfactory in respect of yield and purity of the end product, and does not permit simple and economical operation.

We have found that α-haloethylcarbamyl halides are obtained in an advantageous manner if vinyl isocyanate is reacted with a hydrogen halide at from $-78°$ C. to $+80°$ C.

Further, we have found the novel α-haloethylcarbamyl halides, in particular the novel α-chloroethylcarbamyl chloride.

Where hydrogen chloride is used, the reaction may be represented by the following equation:

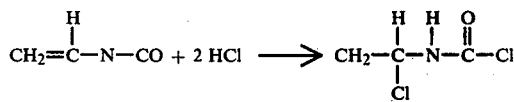

Compared to the conventional process, the process of the invention gives α-haloethylcarbamyl halides more simply and more economically, and in better yield and in greater purity. Working up is substantially simpler since the reaction mixture obtained does not contain a large number of different components. All these advantageous results are surprising, since the formation of a variety of reaction products was to be expected from the great reactivity of the starting materials. It was also to be expected that α,β-unsaturated nitrogen compounds would polymerize or hydrolyze very easily under the influence of acids. For example, N-vinylpyrrolidone is converted to a mixture of oligomers under the influence of even small amounts of an inorganic acid (Ullmanns Encyclopädie der technischen Chemie, volume 14, page 261). Bull. Soc. Chim. Belg., 65 (1956), 291–296 discloses that vinyl isocyanate is hydrolyzed by aqueous 12-normal hydrochloric acid in acetone to give acetaldehyde.

Vinyl isocyanate may be prepared, for example, by reacting acrylyl chloride with sodium azide (Bull. Soc. Chim. Belg., loc. cit.) or by thermally decomposing N-tert.-butyl-N-vinylcarbamyl chloride. The hydrogen halide, advantageously hydrogen bromide and especially hydrogen chloride, is used in the stoichiometric amount or in excess, preferably in an amount of from 2 to 2.2 moles per mole of vinyl isocyanate. The reaction is advantageously carried out at from $+40°$ C. to $-78°$ C., preferably at from $+30°$ C. to $-78°$ C., and especially at from $0°$ C. to $-40°$ C., under atmospheric or superatmospheric pressure, preferably at from 0.7 to 2 bars, continuously or batchwise. The reaction can be carried out in the absence of a solvent, but it is advantageous to use a solvent which is inert under the reaction conditions. Water is not used. Preferably, the reaction is carried out in a solvent which serves as the reaction medium for the further conversion of the end product, especially of α-chloroethylcarbamyl chloride. Examples of suitable solvents are aromatic hydrocarbons, eg. toluene, ethylbenzene, o-, m- and p-xylene, isopropylbenzene and methylnaphthalene; halohydrocarbons, especially chlorohydrocarbons, eg. tetrachloroethylene, 1,1,2,2- or 1,1,1,2-tetrachloroethane, amyl chloride, cyclohexyl chloride, 1,2-dichloropropane, methylene chloride, dichlorobutane, isopropyl bromide, n-propyl bromide, butyl bromide, chloroform, ethyl iodide, propyl iodide, chloronaphthalene, dichloronaphthalene, carbon tetrachloride, 1,1,1- or 1,1,2-trichloroethane, trichloroethylene, pentachloroethane, 1,2-dichloroethane, 1,1-dichloroethane, n-propyl chloride, 1,2-cis-dichloroethylene, n-butyl chloride, 2-, 3- and isobutyl chloride, chlorobenzene, fluorobenzene, bromobenzene, iodobenzene, o-, p- and m-dichlorobenzene, o-, p- and m-dibromobenzene, o-, m- and p-chlorotoluene, 1,2,4-trichlorobenzene, 1,1-dibromodecane and 1,4-dibromobutane; ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and β,β'-dichlorodiethyl ether; ketones, eg. methyl ethyl ketone, acetone, diisopropyl ketone, diethyl ketone, methyl isobutyl ketone, mesityl oxide, acetophenone, cyclohexanone, ethyl isoamyl ketone, diisobutyl ketone, methylcyclohexanone and dimethylcyclohexanone; esters, eg. methyl acetate, n-propyl acetate, methyl propionate, butyl acetate, ethyl formate, methyl phthalate, methyl benzoate, ethyl acetate and phenyl acetate; aliphatic or cycloaliphatic hydrocarbons, eg. pentane, heptane, pinane, nonane, gasoline fractions within a boiling range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane, and octane; and mixtures of these. The solvent is advantageously used in an amount of from 200 to 10,000 percent by weight, preferably from 300 to 2,000 percent by weight, based on the vinyl isocyanate starting material.

The reaction may be carried out as follows: a mixture of the starting materials, advantageously with a solvent, is kept at the reaction temperature for from 0.1 to 4 hours. Advantageously, the vinyl isocyanate is introduced into the solvent and hydrogen halide gas is introduced at the reaction temperature. The reaction solution is then advantageously stirred for from 0.25 to one hour. The end product is then isolated from the mixture in the conventional manner, for example by crystallization and filtration.

The α-haloethylcarbamyl halides, especially α-chloroethylcarbamyl chloride, prepared by the process of the invention, are valuable starting materials for the manufacture of surface-coating raw materials, textile coatings, dyes, drugs and crop protection agents.

In the Examples, parts are by weight.

EXAMPLE 1

69 parts of vinyl isocyanate are introduced into 250 parts of carbon tetrachloride. 73 parts of hydrogen chloride are passed into this solution in the course of one hour at $-35°$ C. The reaction solution is then stirred for a further 15 minutes at the same temperature. After filtering, 137 parts (95% of theory) of α-chloroethylcarbamyl chloride of melting point 21° C. are obtained; the NMR spectrum in CCl$_4$ (with tetramethylsilane as the standard) gives the following:

$(CH_3-)$    1.8 ppm $(Cl-\underset{|}{\overset{|}{C}}-H)$    5.8 ppm $(NH)$    7.5 ppm.

EXAMPLE 2

50 parts of vinyl isocyanate are introduced into 150 parts of methylene chloride. 125 parts of hydrogen bromide are passed into this solution, at −20° C., in the course of 70 minutes. The reaction solution is then stirred for a further 40 minutes at the same temperature. After filtering, 150 parts (90% of theory) of α-bromoethyl carbamyl bromide of melting point 55° C. are obtained; the NMR spectrum in CDCl$_3$ (using tetramethylsilane as the standard) gives:

$(CH_3-)$    2.0 ppm $(Br-\underset{|}{\overset{|}{C}}-H)$    5.9 ppm $(NH)$    6.8 ppm.

We claim:
1. A process for the manufacture of an α-haloethyl-carbamyl halide which comprises:
   reacting vinyl isocyanate with a hydrogen halide in a non-aqueous medium at a temperature of from −78° C. to +80° C.
2. The process of claim 1, wherein the reaction is carried out at from +40° C. to −78° C.
3. The process of claim 1, wherein the reaction is carried out at from +30° C. to −78° C.
4. The process of claim 1, wherein the reaction is carried out at from 0° C. to −40° C.
5. The process of claim 1, wherein the reaction is carried out in the presence of a solvent which is inert under the reaction conditions.

* * * * *